United States Patent [19]

Vasile

[11] 4,232,557
[45] Nov. 11, 1980

[54] PERIODIC MAGNET UNIDIRECTIONAL TRANSDUCER

[75] Inventor: Carmine F. Vasile, Thousand Oaks, Calif.

[73] Assignee: Rockwell International Corporation, El Segundo, Calif.

[21] Appl. No.: 32,057

[22] Filed: Apr. 23, 1979

[51] Int. Cl.³ ............................................. G01N 29/04
[52] U.S. Cl. ........................................ 73/629; 73/643
[58] Field of Search ................. 73/629, 643, 627, 600; 324/238

[56] References Cited
U.S. PATENT DOCUMENTS 4,127,035  11/1978  Vasile ..................................... 73/629

*Primary Examiner*—Anthony V. Ciarlante

*Attorney, Agent, or Firm*—H. Frederick Hamann; Craig O. Malin; John J. Deinken

[57] ABSTRACT

An electromagnetic transducer is provided which transmits and receives ultrasonic waves from a metallic part predominately in only one direction. At least two rows of permanent magnets are placed adjacent each other in a side-by-side relation. The N-S axes of the magnets are substantially parallel and adjacent magnets in each row have opposite polarity so that two periodic magnetic fields are created. The adjacent magnets are off-set by one-fourth period. Coils wrapped around each row of magnets are driven in phase quadrature in order to generate a unidirectional elastic wave in the metallic part. In another embodiment, sets of three rows of magnets are offset by one-sixth period and driven in 60° phase shift.

10 Claims, 4 Drawing Figures

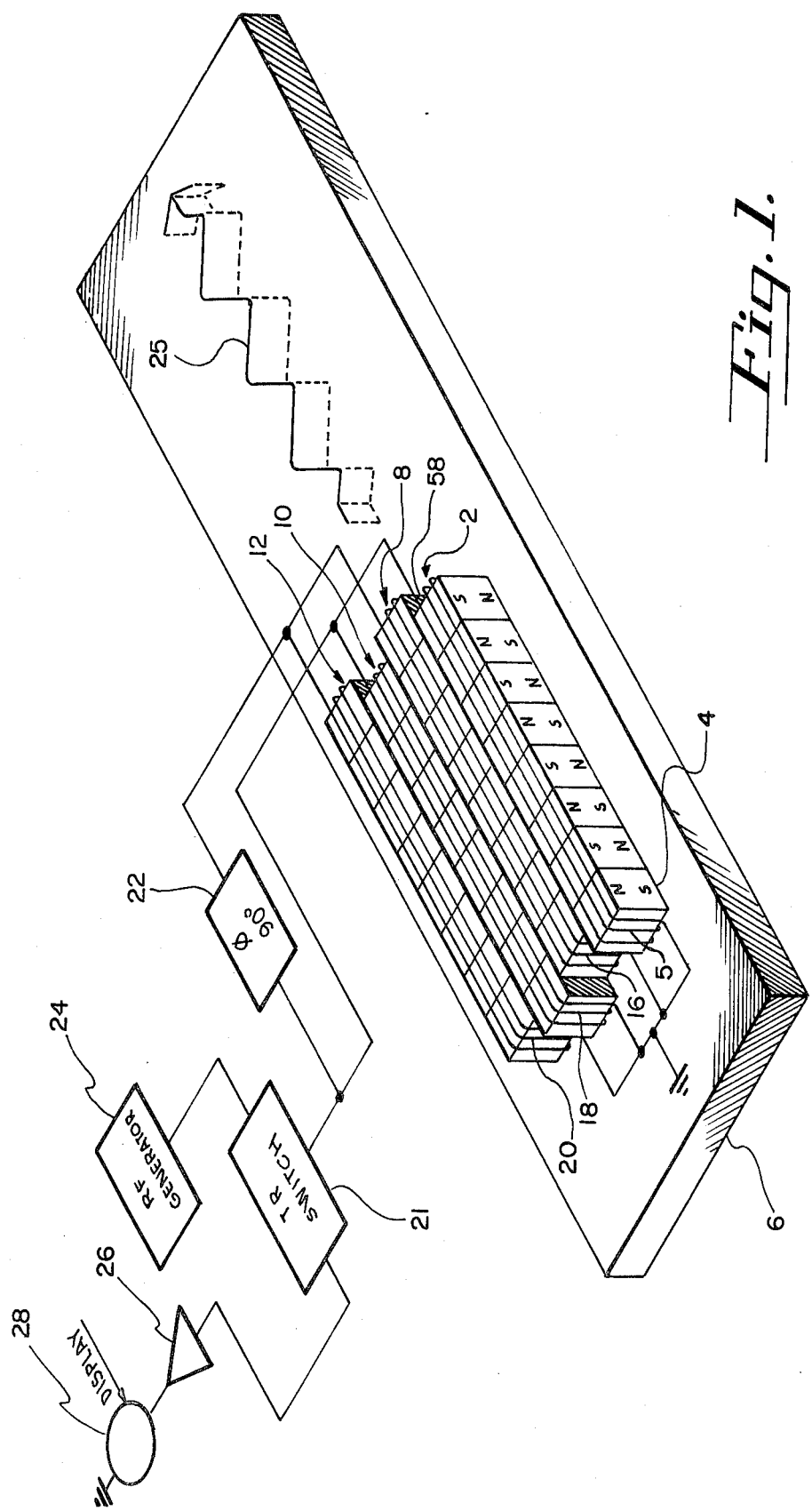

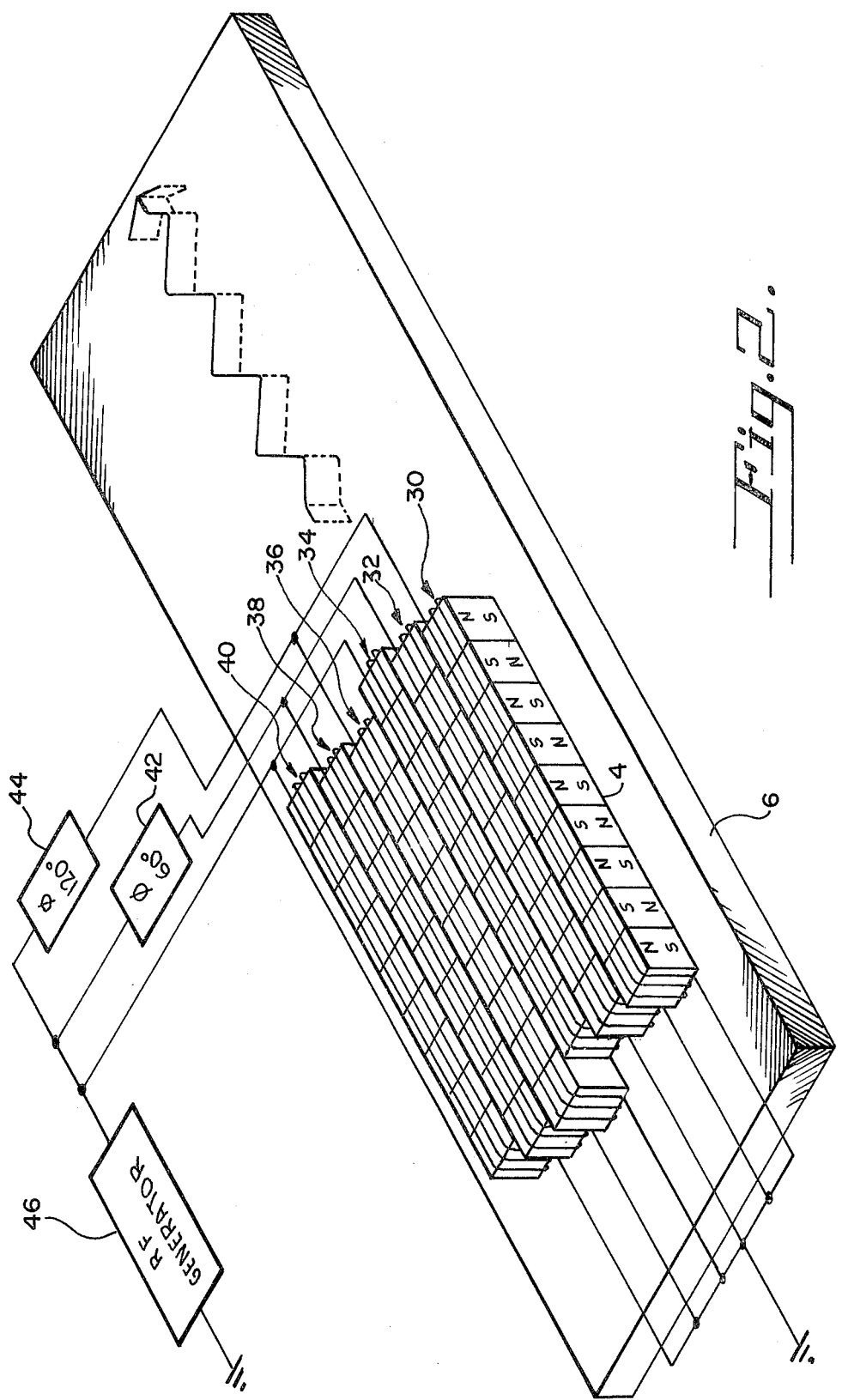

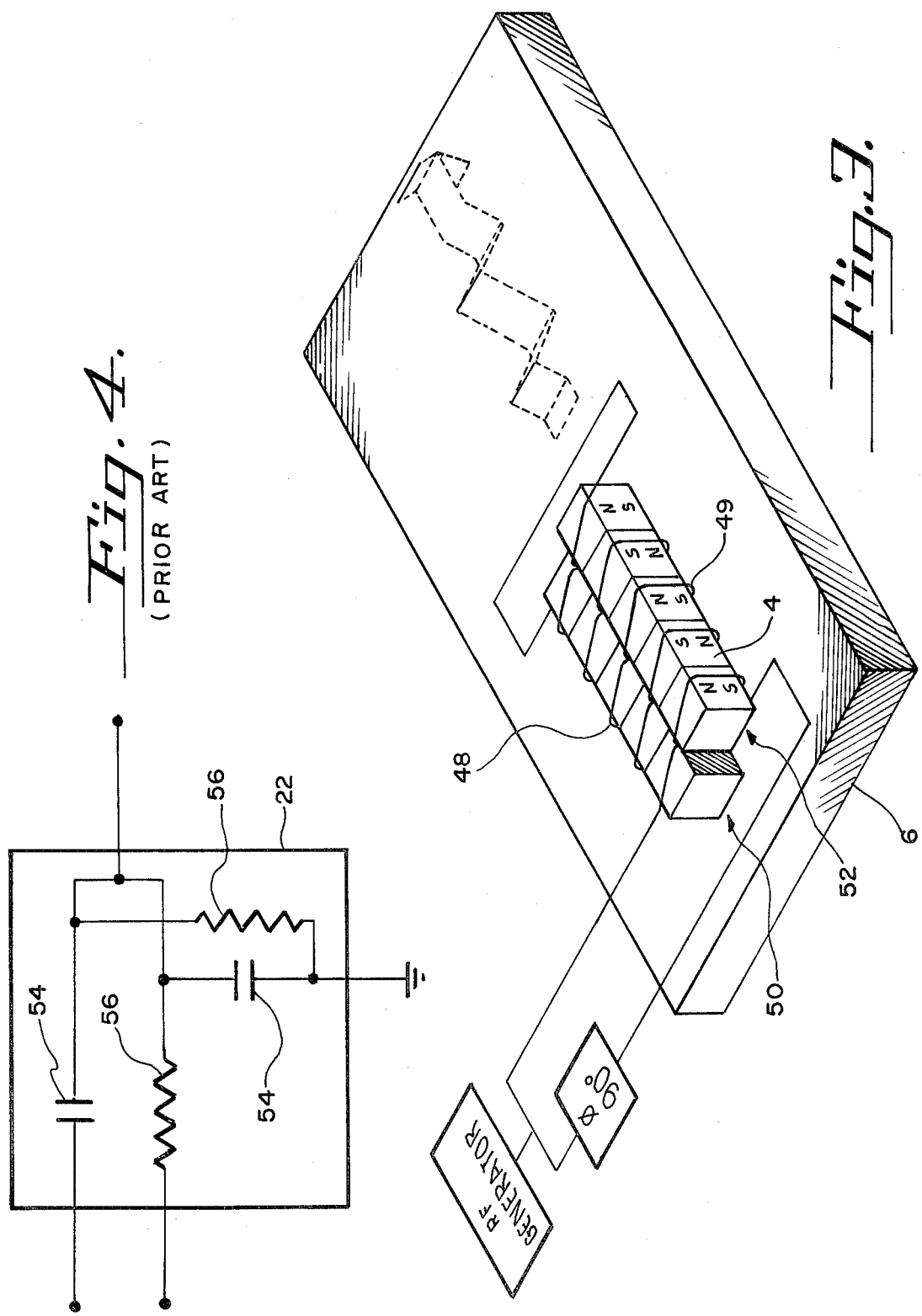

4,232,557

PERIODIC MAGNET UNIDIRECTIONAL TRANSDUCER

STATEMENT OF GOVERNMENT INTEREST

The invention herein described was made in the course of or under a contract or subcontract thereunder, (or grant) with the United States Air Force.

BACKGROUND OF THE INVENTION

1. Field of the Invention

This invention relates to the field of nondestructive testing and particularly to electromagnetic transducers for generating and receiving ultrasonic waves used in ultrasonic inspection of metal parts.

2. Description of the Prior Art

Ultrasonic waves can be generated in conductive materials such as metals by a Lorentz force mechanism using an electromagnetic transducer (EMAT). Such EMAT transducer has a coil which is placed adjacent the surface of the metal and an RF current is fed through the coil. The current in the coil induces eddy currents in the metal which react against an applied static magnetic field to produce the forces that launch the ultrasonic waves.

Recently, a new type of electromagnet transducer has been developed which uses a row of permanent magnets to create a static periodic magnetic field in the material. This periodic magnet EMAT is described in U.S. Pat. Application Ser. No. 830,269, filed Sept. 2, 1977, now U.S. Pat. No. 4,127,035 by Carmine F. Vasile, the inventor of the present unidirectional transducer. When such transducer is used to launch ultrasonic waves parallel to the surface of a metal, at least two waves traveling in opposite directions are generated in the metal. These two waves and their reflections eventually arrive at the receiver and must be identified to interpret the results. This complicates the interpretation of the data and increases the possibility of error.

Further, such prior art multidirectional transducer is less efficient because it emits and receives energy in directions which are not usable, rather than in only a single usable direction.

SUMMARY OF THE INVENTION

It is an object of the invention to provide a periodic magnet unidirectional transducer.

It is an object of the invention to provide a periodic magnet EMAT which transmits ultrasonic waves predominately in one direction.

It is a further object of the invention to provide a periodic magnet EMAT which receives and indicates ultrasonic waves coming predominately from one direction only.

It is an object of the invention to provide a periodic magnet EMAT which transmits and receives ultrasonic waves predominately in one direction only.

It is also an object of this invention to provide a periodic magnet transducer for transmitting and receiving ultrasonic waves which has improved efficiency because ultrasonic waves are transmitted and received predominately in only a preselected direction.

According to the invention, at least two rows of permanent magnets are placed adjacent each other in a side-by-side relation. The N-S axes of the magnets are substantially parallel and adjacent magnets in each row have opposite polarity so that two periodic magnetic fields are created. The adjacent magnets are off-set by one-fourth period. Coils wrapped around each row of magnets are driven in phase quadrature in order to generate a unidirectional elastic wave in the metallic part. In another embodiment, sets of three rows of magnets are off-set by one-sixth period and driven in 60° phase shift.

These and other objects and features of the present invention will be apparent from the following detailed description, taken with reference to the accompanying drawings.

BRIEF DESCRIPTION OF THE DRAWINGS

FIG. 1 is a perspective view of a quadrature-phase embodiment of a unidirectional periodic magnet EMAT and a schematic circuit of related transmitting and receiving electronics for shear-type elastic waves;

FIG. 2 is a partial, perspective view of a three-phase embodiment of a unidirectional periodic magnet EMAT and a schematic circuit of related transmitting electronics for shear-type elastic waves;

FIG. 3 is a perspective view of a quadrature-phase embodiment of a unidirectional periodic magnet EMAT and a schematic of an RF generator for Lamb-type waves; and FIG. 4 is a circuit diagram of a 90° (quadrature) phase shifter.

DESCRIPTION OF THE PREFERRED EMBODIMENT

A typical prior art multi-directional EMAT consists of a single row 2 of individual permanent magnets 4 with a coil 5 wrapped longitudinally around the row as shown by row 2 in FIG. 1. When a suitable RF pulse is sent through coil 5, a shear-type elastic wave is generated in plate 6 as described in U.S. Pat. Application Ser. No. 830,269. Unfortunately, a second elastic wave is also generated in the opposite direction to the first wave. This second wave is reflected from the edge of plate 6 and from discontinuities in the plate, and these reflections make it difficult to interpret the results.

In work leading to the present invention, it was discovered that one of the waves could be greatly suppressed or eliminated if at least two periodic magnet transducers were driven so that the energy radiated in one direction cancels while the energy radiated in the other direction adds. FIG. 1 shows the configuration of a quadrature-phase transducer capable of such cancellation and addition. Although one set of two rows 2, 8 of magnets provides considerable unidirectionality to the transducer, the two sets of four rows 2, 8, 10, 12 shown in FIG. 1 provide even greater unidirectionality.

The individual magnets 4 are of similar size and they are positioned so that adjacent magnets in each row have opposite polarities. Thus, a periodic magnet field is created adjacent to and in metal plate 6. The period of the field is equal to the thickness of two adjacent magnets. Adjacent rows 2, 8 form one set and adjacent rows 10, 12 form a second set. The polarity of magnets 4 in each row is the same except that adjacent rows are shifted linearly one-quarter period. Each set 2, 8 is also shifted by one-quarter period from its adjacent set 10, 12.

Separate coils 5, 16, 18, 20 are wrapped longitudinally around each row 2, 8, 10, 12. One end of each coil is grounded and the other end leads to a transmit-receive switch 21. However, a 90° phase shifter 22 is placed in series with the ends of the coils around dimensionally phase-shifted rows 8, 12.

If the periodic magnet EMAT is to function as a transmitter of elastic waves in plate 6, then the phase-shifted conductor and the other conductor are connected by switch 21 to RF generator 24. Generator 24 passes an RF current through the coils. The current going to the coils around displaced rows 8, 12 are phase shifted 90° by phase shifter 22. This RF current induces eddy currents in plate 6 flowing transversely to the periodic magnetic field. The resulting interaction launches an elastic wave from each row 2, 8, 10, 12 through plate 6 at the same frequency as the RF current. Each wave moves in two opposite directions as it spreads away from the row which launched it.

However, the phase and position of one of the waves is formed so that its amplitude adds to the amplitude of the adjacent wave in one direction and subtracts from the amplitude of the adjacent wave in the opposite direction. Consequently, a substantially unidirectional wave 25 is created as a result of the addition of two separate waves that are properly phased and positioned by the design and operation of the multi-row transducer.

If the transducer is to function as a receiver of elastic wave energy from plate 6, then switch 21 connects the lines from the transducer to amplifier 26 and to a display device 28 such as a cathode ray tube or digital readout. Movement of test material under the transducer as elastic waves are received causes signals to be generated in the transducer, and these signals are amplified in amplifier 26 and displayed on device 28.

FIG. 2 shows a three-phase embodiment of a transducer according to the invention. Rows 30, 32, 34, 36, 38, 40 of permanent magnets 4 are arranged in two separate sets 30, 32, 34 and 36, 38, 40 in a manner similar to the previously described quadrature embodiment except that adjacent rows are offset linearly by one-sixth period. The phase of adjacent rows is shifted 60° by phase-shifters 42, 44. An RF generator 46 is used to drive the transducer as a transmitter of shear-type elastic waves. Alternately, the transducer can be used as a receiver, as previously described for the quadrature-phase transducer.

As shown in FIG. 3, coils 48, 49 can be wound transversely to the length of rows 50, 52 of permanent magnets 4 so that Lamb-type waves are generated in plate 6 rather than shear waves. Rows 50, 52 are shifted by one-quarter period and one coil is phase shifted 90° to provide wave addition so that a substantially unidirectional wave is launched as previously described.

The designs of suitable phase shifters are well known in the electronic art. FIG. 4, for example, shows a simple 90° phase-shifter 22 for the quadrature-phase transducer of FIG. 1. For a transducer operating at 130 KHz, phase shifter 22 comprises two capacitors 54 of 122 pF each and two resistors 56 of 1 Kohms each.

Various modification and designs within the skill of the electronic art can be incorporated into the transducer without departing from the present invention. For example, electromagnetic shields 58 can be placed between the rows of magnets to improve the transducer's performance as shown in FIG. 1. The number of rows of permanent magnets in each set can be varied provided that each row is dimensionally offset from an adjacent row by 1/2n th period and provided that the phase of current in adjacent rows is shifted according to the equation $\Delta\phi = 180/n$, wherein "n" is the number of rows and $\Delta\phi$ is the phase difference of the current in adjacent coils. Further, the number of permanent magnets in each row, their size, and the number of sets can be optimized to meet the design requirements of particular applications.

Accordingly, it should be clearly understood that the form of the present invention described above and shown in the accompanying drawings is illustrative only and is not intended to limit the scope of the present invention.

What is claimed is:

1. A periodic magnet, unidirectional transducer comprising:
   a first row of permanent magnets, the N-S axes of said magnets being substantially parallel, adjacent magnets in said first row having differently oriented polarity so that a first periodic magnetic field is created;
   a second row of permanent magnets, the N-S axes of said magnets being substantially parallel, adjacent magnets in said first row having differently oriented polarity so that a second periodic magnetic field of the same periodicity as said first field is created, said second row being positioned adjacent and parallel to said first row and being offset along its length by one-quarter period from said second row; and
   separate coils around said first and said second rows of magnets.

2. The transducer as claimed in claim 1, wherein said separate coils are wrapped around said rows in the longitudinal direction, whereby the transducer is a shear-wave type transducer.

3. The transducer as claimed in claim 1, wherein said separate coils are wrapped around said rows in the transverse direction, whereby the transducer is a Lamb-wave type transducer.

4. The transducer as claimed in claim 1, including an electromagnetic shield between said first and said second permanent magnets.

5. A periodic magnet, unidirectional transducer comprising:
   a first set of a "n" number of rows of permenent magnets, the N-S axes of said magnets being substantially parallel, adjacent magnets in each of said rows having differently oriented polarity so that each row of magnets creates a periodic magnetic field of the same periodicity and polarity, said rows being adjacent and parallel in side-by-side relation, each row being offset from its adjacent row by "1/2n" th period;
   a second set of a "n" number of rows of permenent magnets, said second set being substantially the same as said first set, said second set being positioned adjacent and parallel tp said first set in side-by-side relation and offset from said first set by "1/2n" th period; and
   a separate coil wrapped around each of said rows of permenent magnets in each of said sets.

6. The periodic magnet undirectional transducer as claimed in claim 5, including an electromagnetic shield between each of said rows of permanent magnets.

7. The periodic magnet, unidirectional transducer as claimed in claim 5, wherein one end of each of said coils is grounded and the other end of each of said coils which is around a spacially in-phase row is connected to a conductor which is common to said spacially in-phase rows.

8. The periodic magnet, unidirectional transducer as claimed in claim 7, including phase shifting means coupled to said conductor to shift the phase of current in adjacent coils by $\Delta\phi = 180°/n$, where $\Delta\phi$ is the difference in phase between said conductors, and n is the number of rows in each of said sets.

9. The periodic magnet, unidirectional transducer as claimed in claim 5, wherein said coil is wrapped around each of said rows in the longitudinal direction, whereby the transducer is a shear-wave type transducer.

10. The periodic magnet, unidirectional transducer as claimed in claim 5, wherein said coil is wrapped around each of said rows in the transverse direction, whereby the transducer is a Lamb-wave type transducer.

* * * * *